United States Patent
Tung et al.

(10) Patent No.: US 11,017,895 B2
(45) Date of Patent: May 25, 2021

(54) IRECON: INTELLIGENT IMAGE RECONSTRUCTION SYSTEM WITH ANTICIPATORY EXECUTION

(71) Applicant: KONINKLIJKE PHILIPS N.V., Eindhoven (NL)

(72) Inventors: Chi-Hua Tung, Aurora, OH (US); Shekhar Dwivedi, Willoughby Hills, OH (US); Yang-Ming Zhu, Solon, OH (US); John Patrick Collins, Cleveland Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 6 days.

(21) Appl. No.: 16/238,613

(22) Filed: Jan. 3, 2019

(65) Prior Publication Data

US 2019/0139271 A1    May 9, 2019

Related U.S. Application Data

(62) Division of application No. 15/326,159, filed as application No. PCT/IB2015/055182 on Jul. 9, 2015, now Pat. No. 10,275,906.

(Continued)

(51) Int. Cl.
*G06K 9/00* (2006.01)
*G16H 30/20* (2018.01)
(Continued)

(52) U.S. Cl.
CPC ......... *G16H 30/20* (2018.01); *G06F 3/04842* (2013.01); *G06F 19/00* (2013.01);
(Continued)

(58) Field of Classification Search
CPC ....... A61B 5/055; A61B 5/002; A61B 5/0046; A61B 5/14551; A61B 5/7267;
(Continued)

(56) References Cited

U.S. PATENT DOCUMENTS 5,866,907 A * 2/1999 Drukier .................. G01N 33/60
250/328
5,977,978 A * 11/1999 Carey ..................... G06T 19/00
345/419

(Continued)

FOREIGN PATENT DOCUMENTS

WO    2009/143346    11/2009
WO    2013/088353    6/2013

*Primary Examiner* — Alex Kok S Liew

(57) ABSTRACT

A diagnostic imaging system retrieves data (206) from a plurality of accessible data sources, the accessible data sources storing data including physiological data describing a subject to be imaged, a nature of a requested diagnostic image, image preferences of a clinician who requested the diagnostic image, and previously reconstructed images of the requested nature of the subject and/or other subjects, reconstruction parameters and/or sub-routines used to reconstruct the previously reconstructed images. The system analyzes (6, 12) the retrieved data to automatically generate reconstruction parameters and/or sub-steps specific to the nature of the requested diagnostic image, the subject, and the clinician image preferences. The system controls a display device (10, 216) to display the generated reconstruction parameters and/or sub-routines to the user for a user selection. The system sets a reconstruction processor system to reconstruct scan data using the selected reconstruction parameters and/or sub-routines.

12 Claims, 7 Drawing Sheets

Related U.S. Application Data

(60) Provisional application No. 62/025,050, filed on Jul. 16, 2014.

(51) Int. Cl.
| | | |
|---|---|---|
| *G16H 40/63* | (2018.01) | |
| *G16Z 99/00* | (2019.01) | |
| *G16H 30/40* | (2018.01) | |
| *G06F 3/0484* | (2013.01) | |
| *G06T 11/00* | (2006.01) | |
| *G06F 19/00* | (2018.01) | |

(52) U.S. Cl.
CPC ........... *G06T 11/003* (2013.01); *G16H 30/40* (2018.01); *G16H 40/63* (2018.01); *G16Z 99/00* (2019.02); *G06T 2210/41* (2013.01)

(58) Field of Classification Search
CPC ......... A61B 6/032; A61B 6/037; A61B 6/486; A61B 6/5217; A61B 8/5223; A61B 5/4064; A61B 5/4076; A61B 5/417; A61B 6/027; A61B 6/4258; A61B 6/481; A61B 6/482; A61B 6/488; A61B 6/504; A61B 6/025; A61B 6/583; A61B 8/483; A61B 6/4266; A61B 6/503; A61B 6/545; A61B 6/547; A61B 6/469; A61B 6/563; A61B 6/466; A61B 6/5258; A61B 6/4085; A61B 6/02; A61B 6/405; A61B 6/4233; A61B 6/4291; A61B 6/5205; A61B 6/542; A61B 5/0073; A61B 5/415; A61B 5/416; A61B 5/418; A61B 5/7285; A61B 6/06; A61B 6/14; A61B 6/4035; A61B 6/5264; A61B 6/541; G01R 33/283; G01R 33/3692; G06T 2207/10081; G06T 2207/20081; G06T 2200/24; G06T 2207/10072; G06T 2207/10116; G06T 2207/20104; G06T 2207/30004; G06T 2207/30032; G06T 2207/30064; G06T 7/0012; G06T 7/20; G06T 7/30; G06T 11/005; G06T 11/006; G01T 1/1603; G01T 1/161; G01T 1/1642; G01T 1/1648; G01T 1/17; G01T 1/2008; G01T 1/204; G01T 1/208; G01T 1/2985; G01T 7/08; G01T 11/006; G06Q 10/10; G06Q 50/22; G06Q 50/24; G06Q 10/00; G06Q 10/06395; G06Q 10/06398; G06Q 30/0202; G06F 19/321; G06F 19/00; G06F 19/327; G06F 19/3425; G06F 19/345; G06F 19/3487; G09B 23/28; Y02A 90/22; Y02A 90/26; G01N 2223/419; G01N 23/046; G01N 33/60; G16H 10/60; Y10S 436/804; Y10S 436/807; Y10T 436/13
USPC ........ 382/128, 131, 132, 248, 325; 250/369, 250/395
See application file for complete search history.

(56) References Cited

U.S. PATENT DOCUMENTS

| | | | |
|---|---|---|---|
| 6,239,438 B1* | 5/2001 | Schubert | ................... G01T 1/17 |
| | | | 250/363.02 |
| 6,650,339 B1* | 11/2003 | Silva | ...................... G06F 3/0481 |
| | | | 345/619 |
| 7,599,534 B2* | 10/2009 | Krishnan | ............... G06T 7/0012 |
| | | | 382/128 |
| 7,653,228 B2 | 1/2010 | Katscher | |
| 8,170,315 B2 | 5/2012 | Mistretta | |
| 8,374,413 B2 | 2/2013 | Chen | |
| 8,445,851 B2* | 5/2013 | Rousso | ................... A61B 5/417 |
| | | | 250/363.02 |
| 8,558,176 B2 | 10/2013 | Komori | |
| 2004/0122706 A1* | 6/2004 | Walker | ................... G06Q 50/22 |
| | | | 705/2 |
| 2004/0122707 A1* | 6/2004 | Sabol | ...................... G06Q 50/22 |
| | | | 705/2 |
| 2004/0122709 A1* | 6/2004 | Avinash | ................ G16H 10/60 |
| | | | 705/2 |
| 2008/0056550 A1* | 3/2008 | Kadir | ...................... G06T 11/006 |
| | | | 382/131 |
| 2008/0108895 A1* | 5/2008 | Sabol | ................... G01N 23/044 |
| | | | 600/425 |
| 2008/0130972 A1* | 6/2008 | Miller | ....................... G06T 7/30 |
| | | | 382/131 |
| 2008/0199063 A1* | 8/2008 | O'Halloran | ........... G06T 11/006 |
| | | | 382/131 |
| 2010/0195892 A1* | 8/2010 | Sato | ....................... G06F 19/321 |
| | | | 382/132 |
| 2012/0148125 A1 | 6/2012 | Dekel | |
| 2012/0271840 A1* | 10/2012 | Vosniak | ................. G16H 50/20 |
| | | | 707/758 |
| 2013/0129165 A1 | 5/2013 | Dekel | |
| 2014/0029818 A1 | 1/2014 | McCoy | |
| 2014/0063449 A1 | 3/2014 | Inoue | |
| 2014/0151563 A1* | 6/2014 | Rousso | ................... G01T 1/161 |
| | | | 250/362 |
| 2014/0163368 A1* | 6/2014 | Rousso | ................... G01T 1/1615 |
| | | | 600/436 |
| 2014/0187932 A1* | 7/2014 | Li | ........................... A61B 6/481 |
| | | | 600/431 |
| 2014/0201126 A1* | 7/2014 | Zadeh | ................... A61B 5/165 |
| | | | 706/52 |
| 2018/0144466 A1* | 5/2018 | Hsieh | ..................... G06T 7/0012 |
| 2018/0303449 A1* | 10/2018 | Zhu | ....................... A61B 6/545 |

* cited by examiner

IRECON: INTELLIGENT IMAGE RECONSTRUCTION SYSTEM WITH ANTICIPATORY EXECUTION

CROSS REFERENCE TO RELATED APPLICATIONS

This application a divisional of U.S. patent application Ser. No. 15/326,159 filed Jan. 13, 2017, which is the U.S. National Phase application under 35 U.S.C. § 371 of International Application No. PCT/IB2015/055182, filed Jul. 9, 2015, published as WO2016/009309 on Jan. 21, 2016, which claims the benefit of U.S. Provisional Patent Application No. 62/025,050 filed Jul. 16, 2014. These applications are hereby incorporated by reference herein.

The present application relates generally to medical imaging. It finds particular application in conjunction image reconstruction, and will be described with particular reference thereto. However, it is to be understood that it also finds application in other usage scenarios and is not necessarily limited to the aforementioned application.

Current image reconstruction systems use a "one approach fits all" strategy, i.e., the reconstruction algorithms or processes are the same for all patients, regardless their demographics, medical history, disease of interest, scan conditions, and etc. It is difficult to achieve consistent and optimal image quality even from data of the same patient if the patient characteristics and scan conditions vary. Some systems are closed and technicians cannot change any reconstruction settings or configurations. Other systems allow technicians to tune the system or algorithm parameters; however, the systems do not guide the technicians to how and what to adjust. To achieve the optimal image quality and improve patient care, a reconstruction system behaviour should adapt to patient unique circumstances and characteristics. Personalized medicine represents the trend in medical decision, practice, and products. Big data is playing an increasingly significant role in medical practice, with improvement in dataset availability, and advances in data mining, machine learning and artificial intelligence.

An intelligent reconstruction system is needed that recommends the parameter settings for image reconstruction techniques to deliver personalized optimal image quality. The present application discloses a reconstruction system that learns, anticipates and adapts to the evolving clinician preferences by proactively recommending reconstruction parameters to improve the workflow efficiency and maximally utilize the computing resources.

In accordance with one aspect, a diagnostic image generating system comprising one or more processors configured to retrieve data from a plurality of accessible data sources, the accessible data sources storing data including physiological data describing a subject to be imaged, a nature of a requested diagnostic image, image preferences of a clinician who requested the diagnostic image, and previously reconstructed images of the requested nature of the subject and/or other subjects, reconstruction parameters and/or subroutines used to reconstruct the previously reconstructed images. The processors are configured to analyze the retrieved data to automatically select reconstruction parameters and/or sub-steps specific to the nature of the requested diagnostic image, the subject and the clinician image preferences. The processors are further configured to control a display device to display the selected reconstruction parameters and/or sub-routines and/or set a reconstruction processor system to reconstruct scan data using the selected reconstruction parameters and/or sub-routines.

In accordance with another aspect, an iRecon system having one or more processors configured to select goals for a final image and generate a plurality of candidate reconstruction algorithms, parameters, filters, and/or sub-steps for reaching the goal. The processors are further configured to access a database having data of at least one of: an electronic medical record, a patient diagnosis, and/or similar patient records and generate alternative reconstruction algorithms, parameters, filters, and/or sub-steps according to the accessed data of the database, where each meets the goals for the final image.

In accordance with another aspect, a method for recommending reconstruction parameters, includes registering a patient for an imaging scan and collecting data from a plurality of data sources. The method further includes designing a patient specific reconstruction system to recommend a set of reconstruction parameters to a technician for reconstructing an image from the imaging scan of the patient based on the collected data and using the designed reconstruction system, generating a plurality of alternate sets of reconstruction parameters according to different reconstruction objectives, the reconstruction objectives including at least one of algorithmic additives, dynamic acquisition controls, technician preferences, and/or scan specific parameters. The method further includes generating a preview image for each set of reconstruction parameters, wherein the preview image depicts the expected image quality using sample images from a database that are associated with a set of reconstruction parameters; displaying the preview images on a display; and receiving a selection of a preview image from a technician using the display.

In accordance with another aspect, a reconstruction route generator, includes a data collector configured to compile at least one of: scan specific data, acquisition parameters, technician preferences, diagnostic data, previous reconstruction data and/or previous reconstructed images representing reconstruction routes; a data processor configured to adapt the system according to the compiled data for a specific patient. The reconstruction route generator further includes an anticipation module configured to use the trained data to create and predict a plurality of reconstruction routes, each reconstruction route anticipating a change to at least one reconstruction parameter affecting the final reconstruction of scanned patient imaging data, wherein the anticipation is based on optimization, a weighted technician preference, alternate algorithm, and/or alternate filter; and an interactive GUI configured to display the plurality of reconstruction routes to a user and further configured to accept a user input.

One advantage resides in personalized reconstruction imaging for patients.

Another advantage resides in more efficient decisions for imaging reconstruction settings.

Still further advantages of the present invention will be appreciated to those of ordinary skill in the art upon reading and understand the following detailed description The invention may take form in various components and arrangements of components, and in various steps and arrangements of steps. The drawings are only for purposes of illustrating the preferred embodiments and are not to be construed as limiting the invention.

FIG. 1 diagrammatically depicts an intelligent image reconstruction system.

Figure 5:
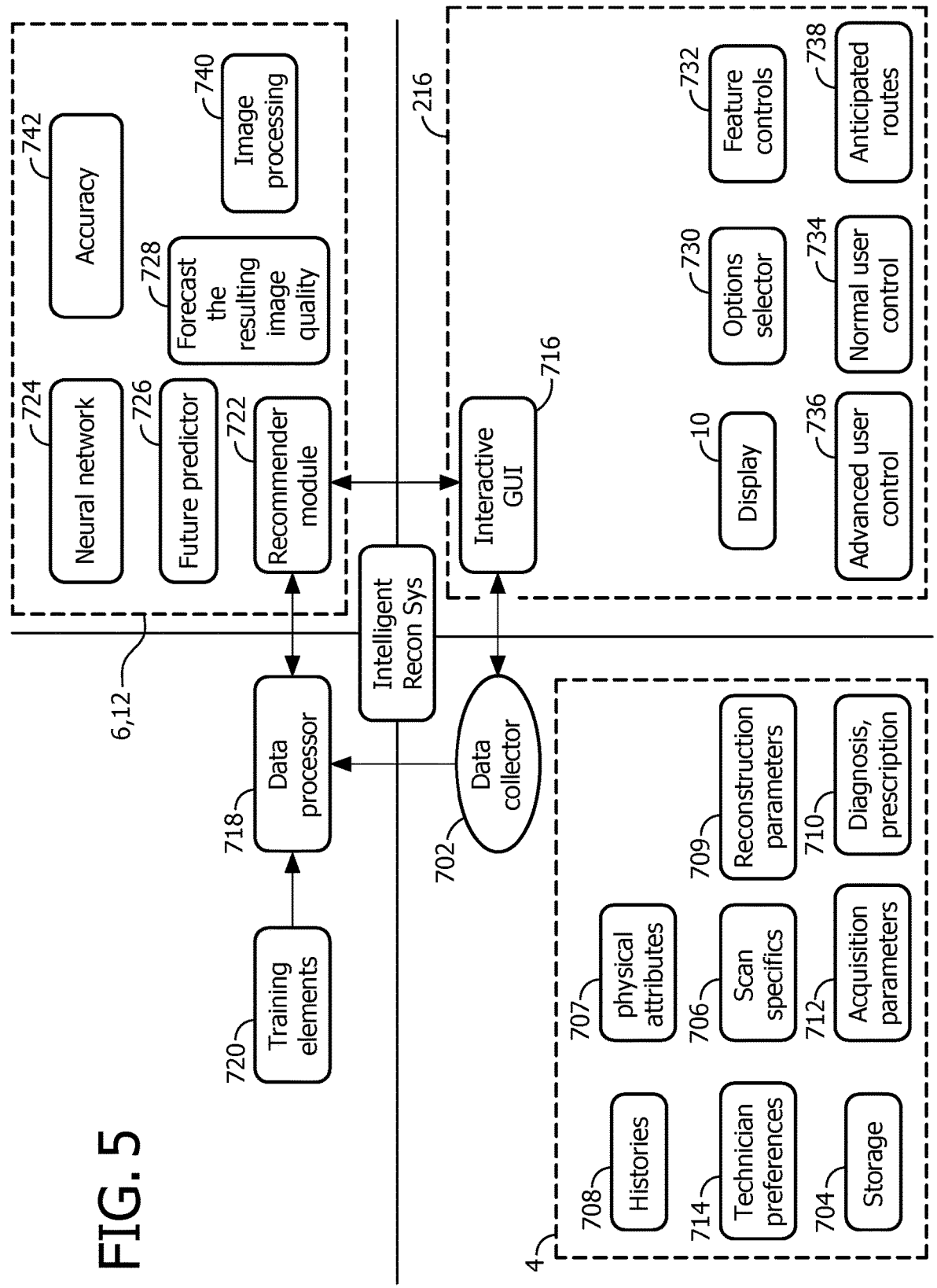

FIG. 5 diagrammatically depicts an alternative modular view of an intelligent reconstruction system.

Figure 6:
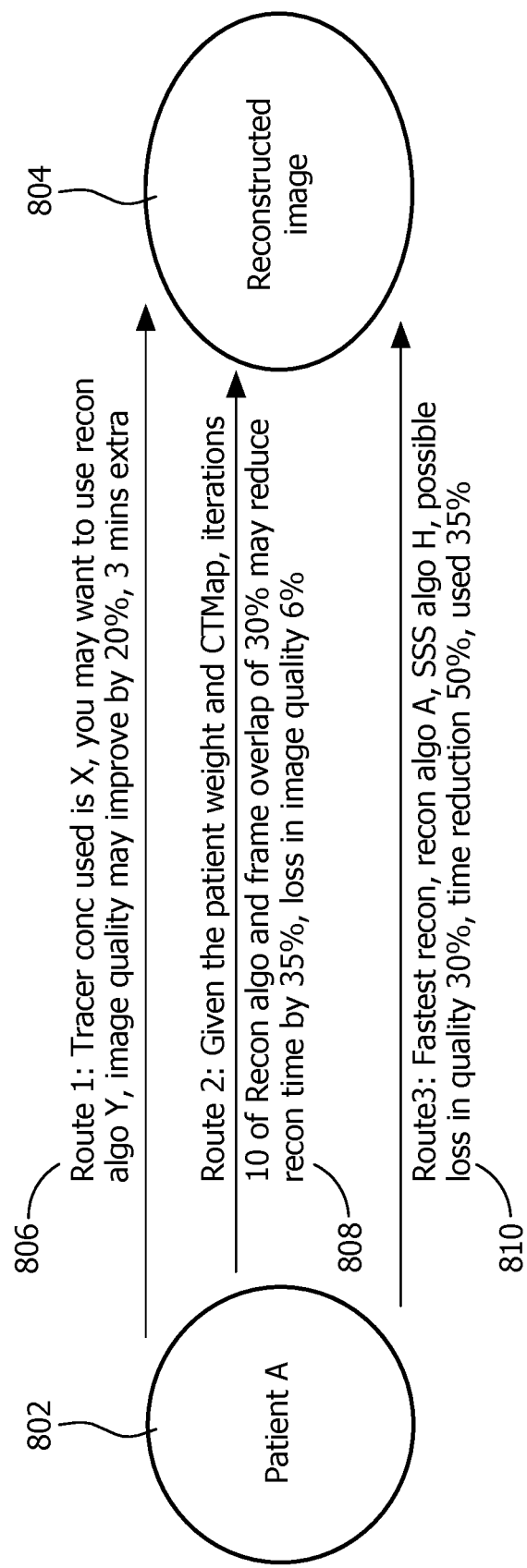

FIG. 6 depicts possible reconstruction routes displayed to a technician.

Figure 7:
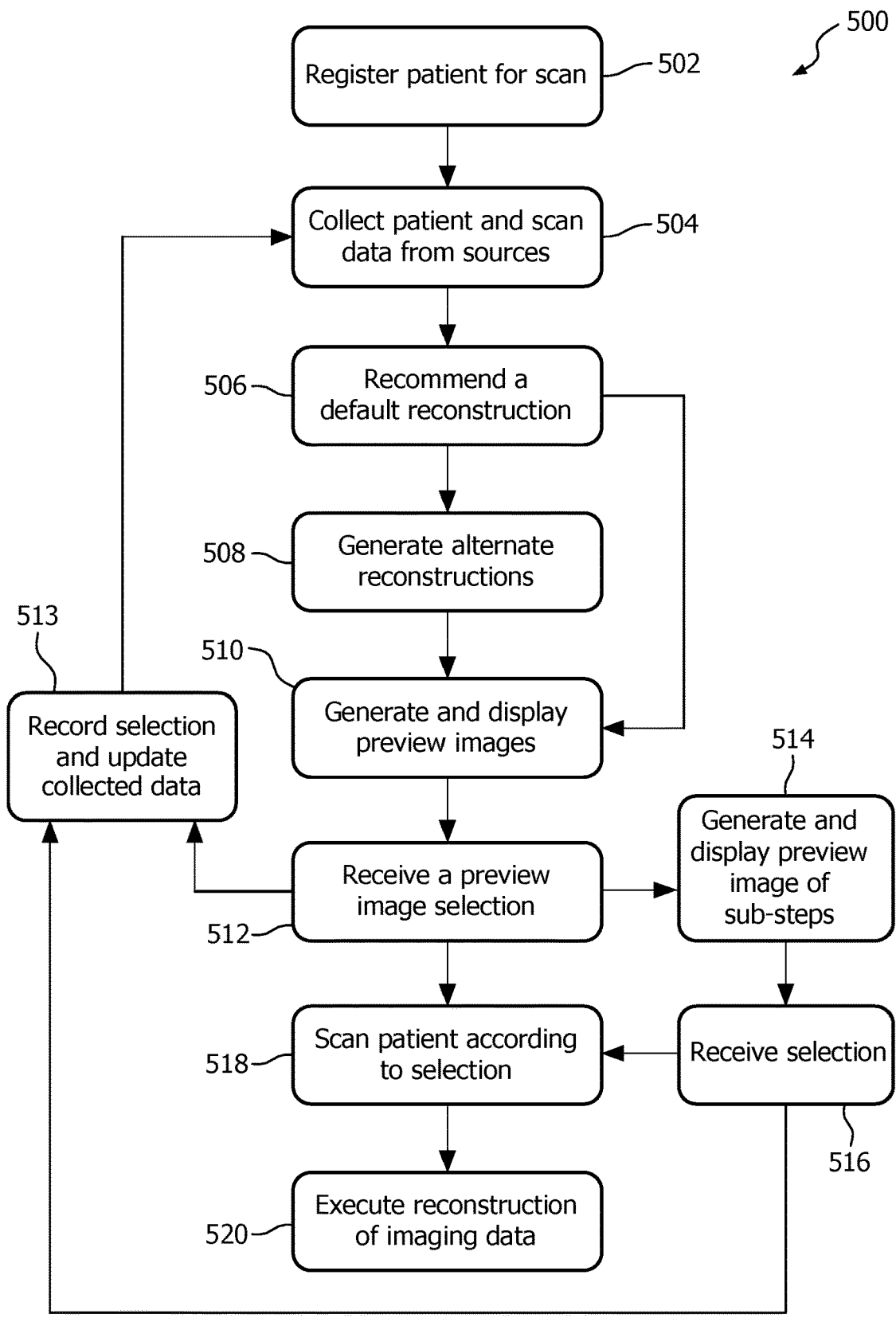

FIG. 7 illustrates a method for intelligent image reconstruction.

Figure 1:
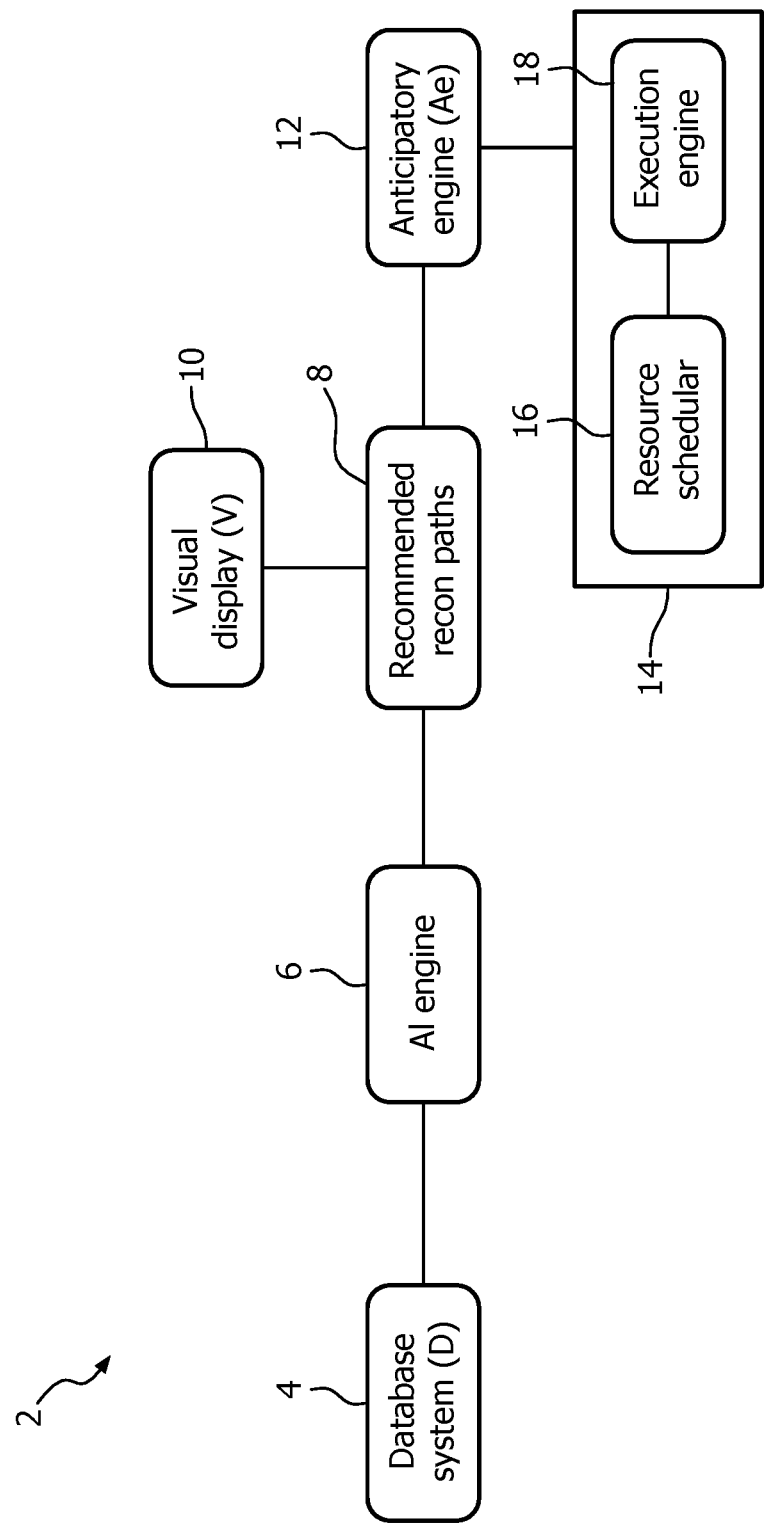

With reference to FIG. 1, a reconstruction system 2 includes a database system 4 having one or more processors that collects and maintains the existing patient, scan, and reconstruction information from an institution, medical system, group of institutions and the like and processes the data for intelligent reconstruction of scanned imaging data. An institution can be the reconstruction system, an office, a hospital, a clinic, a medical care system, or the like. The database system 4 collects or retrieves information from many sources to create a hierarchy of information levels, discussed in greater detail below, used for image reconstruction. In one embodiment, information is directly entered into the database system 4.

Figure 2:
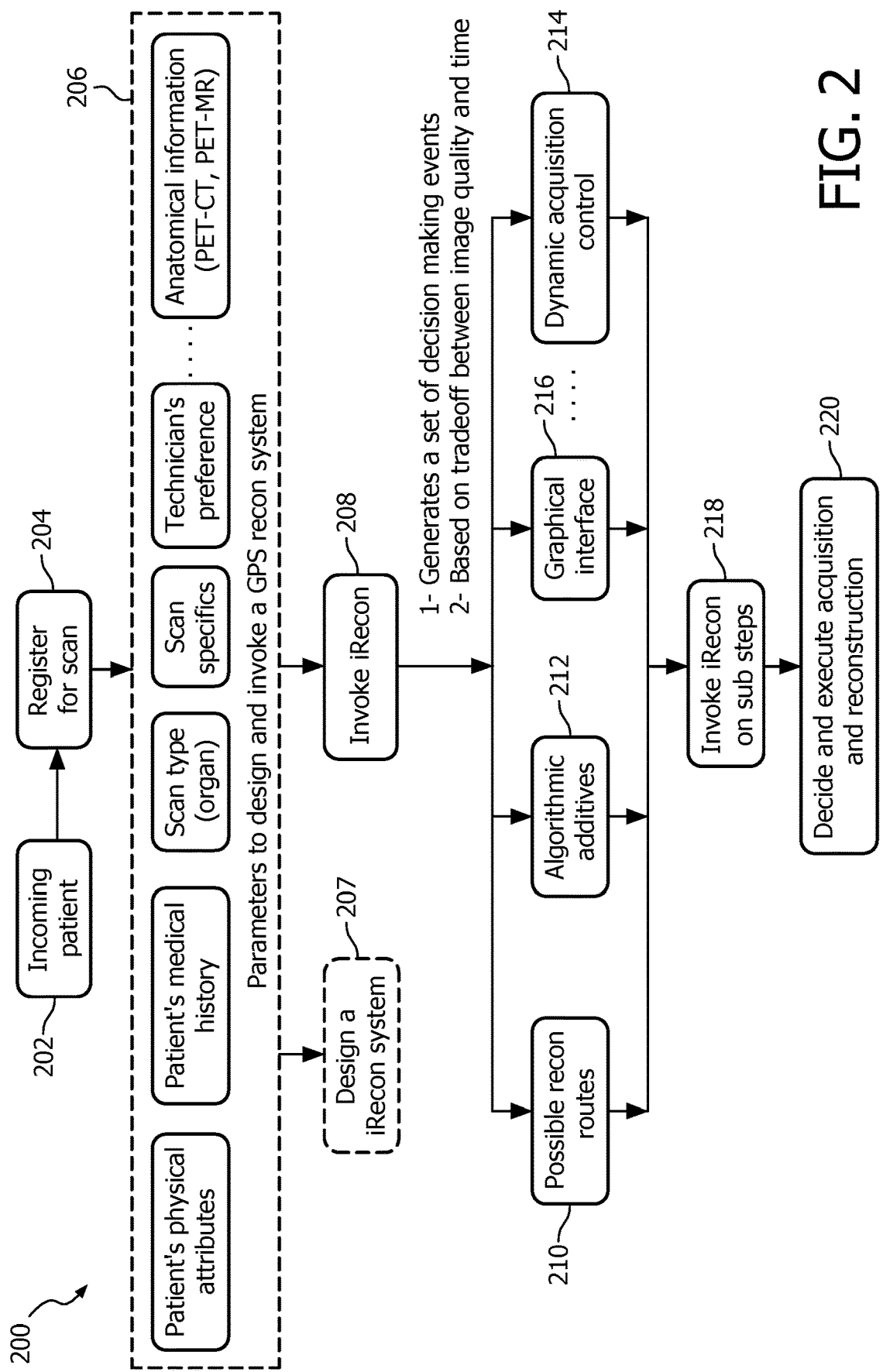
FIG. 2 depicts a workflow for reconstructing images using the system.

With reference to FIG. 2, and continuing reference to FIG. 1, a representative workflow 200 for acquiring and reconstructing patient image data is depicted. When the database system 4 recognizes an incoming patient 202, the database system 4 registers the patient for an imaging scan 204. The database system 4 accesses the collected data as well as any new data, such as patient specific data. The database system 4 collects and maintains patient demographics, medical history and conditions. The database system 4 interfaces with or includes electronic medical records (EMR), patient health records (PHR), or other similar health and wellness data repositories. In one embodiment, the database system 4 collects information from a radiology information system (RIS), health information system (HIS), or other sources. The database system 4 performs data reconciliation for data coming from different sources.

In one embodiment, the database system 4 stores patient medical histories for every patient in the institution. The patient medical histories include previous reconstructed images of patient images and the reconstruction parameters used for the reconstructions. The previous reconstructed images can be used to generate sample preview images of selected reconstruction parameters described in further detail below.

The database system 4 sorts 206 the collected data into different types of data such as: the patient's physical attributes, patient's medical history, the type of scan i.e. organ, scan specific parameters, quantitative numbers, technician preferences, and/or anatomical information i.e. PET-CT, PET-MR. The patient's attributes and medical history include physiological parameters such as age, weight, and height. The type of scan details includes organ(s) involved, imaging modality, the reconstruction protocol, desired bed speed, desired frame overlap, and the like. The scan details include dose limitation, type of isotope, type of tracer, acquisition time limitations, reconstruction time limitations, and the like. It is appreciated that other types of data can be included and sorted by the database system 4.

The database system 4 receives reconstruction goals that the scan of the patient should achieve. The database system 4 receives a past diagnosis or prescription from the technician which factors into the type of scan required for the patient. In one embodiment, the database system 4 stores the information on one or more computer readable storage mediums.

The database system 4 records technician preferences for reconstructing patient images. The database system 4 stores reconstruction parameters that achieve a desirable image quality approved by a technician. The database system 4 records changes a technician makes to the reconstruction parameters in addition to the previous reconstruction parameters that the technician has input. The database system 4 also records the alternatives the technician considers. The database system 4 adapts to the technician preferences when the technician uses the system over time. In one embodiment, the technician preferences are changes made to a default reconstruction plan, a recommended plan, or settings that are favored by the technician that are predicted by the database system 4 over time. As part of the favored settings, the technician preferences include the type of reconstruction algorithm preferred, the type of filters preferred, and the characteristics for the end image such as sharper, smoother, noise characteristics, and the like.

The database system 4 arranges the technician preferences according to a determined hierarchy, e.g. medical network, hospital or clinic site, physicians, and the like. The technician preferences are described using a rules engine. The database system 4 employs fuzzy logic and the like to code each technician preference and remove ambiguities in natural languages. The database system 4 is mined when the system is not in peak use, e.g. at night for the reconstruction parameters that achieve optimal image quality in various situations. The database system 4 records when a default setting is altered by the technician as a technician preference over the default setting. For example, for the same patient, if a specific reconstruction parameter is altered multiple times, the most recent setting from which the image was reconstructed is weighted more heavily and persisted. In one embodiment, the database is a SQL or non-SQL database to manage a plurality of datasets in the database system 4.

An artificial intelligence (AI) engine 6 accesses the database system 4 via a neural network or the like when a technician begins using the intelligent reconstruction system for a specific patient scan. The AI engine 6 includes at least one processor for computing recommended reconstruction parameters. The AI engine 6 constructs 207 an iRecon system 208 from the database system 4 that is specific to the patient and the patient scan. Like a Global Positioning System, the iRecon system 208 offers the technician a plurality of reconstruction parameters/options or routes to the desired reconstruction goal. The iRecon system 208 includes scan specific data from the database system 4 that is used by the AI engine 6 to recommend reconstruction parameters, i.e. a route to the reconstruction goal and optional alternate routes if applicable. The data contained in the iRecon system 208 is fit to the patient with different types of data such as patient medical history, patient details, type of scan, scan specifics, and technician preferences. The iRecon system 208 takes the reconstruction goals and automatically generates reconstruction and acquisition decision-making parameters for the technician as an initial recommendation, i.e. a starting point.

The AI engine 6 employs a hierarchy based on the amount of data available to construct the iRecon system 207. In one embodiment, the AI engine 6 employs a three-tiered hierarchy to classify the system based on amount of data available, i.e. no data, medium amount of data, or lots of data.

In the instance where the database system 4 contains no data, e.g. an initial startup state, the AI engine 6 adapts to recommend a default set of reconstruction parameters based on other information. In one embodiment, the AI engine 6 recommends a reconstruction parameter using a preference-based system. The preference-based system can be rule-based using a built-in fuzzy logic. For example, a rule can be to use a reconstruction with specific settings for a patient with a high weight. In another embodiment, the AI engine 6 uses a Bayesian network that codifies expert knowledge of reconstruction algorithms or workflows are deployed, when patient demographics are used as input and a maximum a posteriori (MAP) estimate of the recon setting is the output.

When the database system 4 contains a medium amount of data, e.g. when some data has been accumulated by the database system 4 from a source, the AI engine 6 uses the available data to automatically recommend reconstruction parameters. In one embodiment, the AI engine 6 uses case-based reasoning. Using case-based reasoning, patient demographics and other medical conditions are coded as a vector that is compared to the vectors of already collected patients. Among the patient vectors, the AI engine 6 determines the top closest vectors, and the reconstruction parameters used for those top matching patients are used as a recommendation to a technician. When seeking the closest patient vectors, the AI engine 6 calculates various similarity metrics and each element is weighted differently. In one embodiment, the similarity metrics are based on Euclidean distance, or information theoretic.

When the database system 4 contains a large volume of data, the AI engine 6 uses a learning-based approach. The AI engine 6 uses patient data in the database system 4 to regress a math model. The AI engine 6 feeds the new incoming patient data into the math model, and calculates reconstruction parameters. In one embodiment, the AI engine 6 uses a neural network to fit the data from the database system 4, where the input layer includes patient data and the output layer is the recommended reconstruction parameters. In another embodiment, a support vector machine (SVM) is used to compute the recommended reconstruction parameters.

Using the reconstruction parameters from the AI engine 6, an anticipatory engine (AE) 12 creates a plurality of alternate reconstruction parameters. In one embodiment, the alternate reconstruction parameters are based on the technician preferences from which the technician can select. The plurality of alternate reconstruction parameters can be changes that the AE 12 anticipates the technician will most likely make. The anticipation is based on technician specific preferences built as the technician uses the system such that the technician's tendencies are anticipated, i.e. predicted, automatically by the system. In another embodiment, the alternate reconstruction parameters are based on an optimization, patient demographics, scan goals, patient demographics, and/or specific reconstruction parameters to be used. The AE 12 invokes the iRecon system 208 to create different sets of reconstruction parameters. The iRecon system 208 generates a set of decision-making events and creates alternative reconstruction parameters. The iRecon system 208 adapts to the technician's and the patient's needs and requirements by tuning the reconstruction pipeline based on input parameters given by the technician. The iRecon system 208 optimizes the reconstruction workflow for the best image quality in a set of given conditions rather than a default image quality. The iRecon system 208 generates alternative reconstruction parameters 210 to present to the technician. The technician can optionally select the default recommended reconstruction parameters or adapt the reconstruction plan to the suggestions by iRecon system 208. Recommendations from iRecon system 208 include tradeoffs in terms of quality and speed. For example, one recommendation has a quicker acquisition and quick reconstruction but with certain compromise on image quality while another recommendation gives a better image quality at the expense of time taken in acquisition and reconstruction. The technician decides the selection based on his preferences and the criticality of the incoming patient. The database system 4 monitors and records each selection by the technician to be interpreted during future reconstruction planning as part of the technician preferences. In one embodiment, a technician specific profile is created on the database system 4 that includes every selection, i.e. any change to a recommended or default reconstruction, the technician makes over time. The technician specific profile is accessed and the recommendation is weighted toward the selections of the technician profile.

The iRecon system 208 provides the technician with a smart system having flexibility rather than a system that does just one acquisition and one reconstruction irrespective of whichever patient, protocol, organ, tracer used. The iRecon system 208 includes further sub-steps after an initial selection of reconstruction parameters. In one embodiment, the iRecon system 208 recommends algorithmic additives 212 to the technician. For example, if a dose is not optimized for a patient's weight, the iRecon system 208 suggests a different set of filters to improve the image quality. In another example, the iRecon system 208 recommends a smoothing additive for the patient that results in a better image quality, or suggests a different reconstruction algorithm based on the tracer information. The iRecon system 208 generates the additives based on the information given by the technician in terms of acquisition and reconstruction goals.

The iRecon system 208 recommends dynamic acquisition controls 214 to the technician that detail the mode of acquiring imaging data from the patient. The dynamic acquisition controls 214 directly affect image quality and acquisition time. The dynamic acquisition controls 214 dictate the physiological options of scanning the patient such as bed speed and/or patient orientation. The dynamic acquisition controls 214 reduce acquisition time and give more command over the acquisition to the technician. For example, the iRecon system 208 recommends an optimal bed speed, or an amount of overlap between frames for the best image quality. The iRecon system 208 can also recommend dynamically updating the speed of the bed when scanning certain portions of the body that are not of concern according to the diagnosis in the database system 4 and/or the purpose of the scan.

Figure 3:
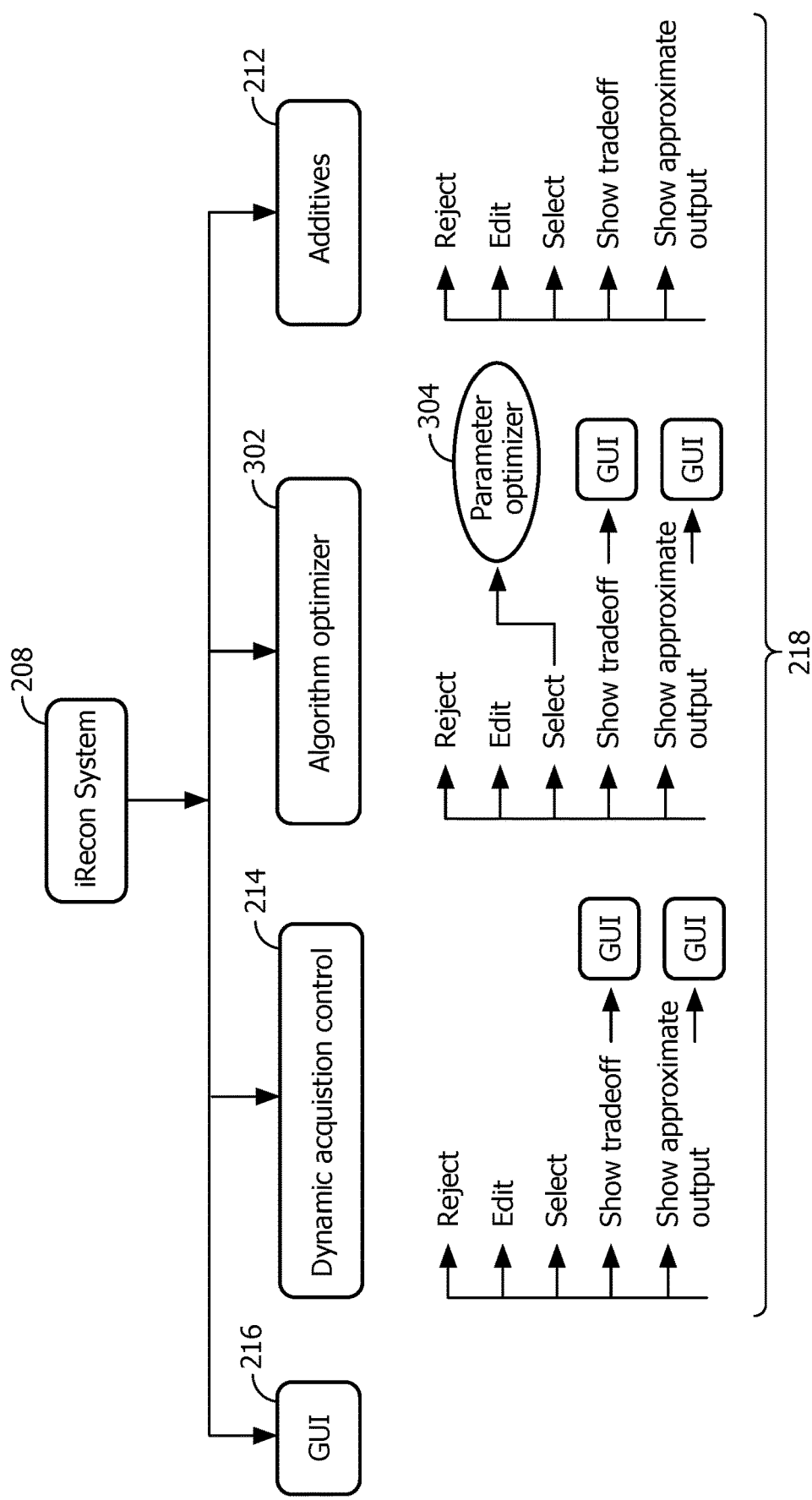
FIG. 3 depicts sub-steps and sub-systems to further tune and analyze a recommended reconstruction and acquisition.

An optimal reconstruction and acquisition can also be demonstrated to the technician in terms of a graphical user interface 216. After generating the alternative sets of reconstruction parameters, the AE 12 can invoke the iRecon system 208 to analyze sub-steps of the reconstruction to provide further alternatives to the technician. With reference to FIG. 3, the technician can go to any sub-step 218 in the graphical user interface 216 and invoke more detailed analysis on the sub-step 218. Each of these outputs can be further designed to give more control to the technician. The technician either ignores, rejects, edits, or selects any of the sub-steps 218 where the default is used for an ignored sub-step 218. If the technician edits or selects a sub-step 218, the edit or selection is optionally recorded as a technician preference by the database system 4.

A sub-step can be selecting a specific reconstruction algorithm. A reconstruction algorithm optimizer 302 suggests optimum reconstruction and filter algorithms to the technician. The technician may select or ignore the suggestions by the iRecon system 208. In the case the technician selects the iRecon system's 208 recommendations; a reconstruction parameter optimizer 304 is invoked to further optimize the reconstruction. The reconstruction parameter optimizer 304 suggests an optimum set of parameters to be applied to the reconstruction algorithm for a given patient. Another sub-step can be selecting a specific filter to be used for reconstruction.

For example, if the technician selects a reconstruction algorithm A, technician can invoke the iRecon system 208 to recommend an optimal set(s) of parameters for the particular case that can be applied using the reconstruction algorithm A. The technician can exercise a personal decision once the iRecon system 208 recommends the optimal parameters, such as optimal filters that work with the selected reconstruction algorithm A. The reconstruction algorithm selection is recorded by the database system 4 to help anticipate subsequent reconstructions for this patient and/or any future patient.

In one embodiment, the AE 12 invokes the iRecon system 208 to use the recommended reconstruction parameters 8 to reconstruct a plurality of preview images that are presented to the technician. Based on prior training, the iRecon system 208 can also provide a preview image of the expected output if each of a plurality of reconstructions is selected by the technician. The preview enhances the decision-making capability of technician. The iRecon system 208 can also recommend the technician select a bed speed and/or frame overlap and show the related tradeoffs in terms of image quality or the end result. Each preview image is associated with a distinct set of reconstruction parameters. From the plurality of preview images, the technician selects the preview image that most closely resembles the technician's desired output image. The preview image makes the technician aware of the end image quality before scanning the patient and/or before reconstructing the images. In one embodiment, the technician has the option to use a set of defined tools, e.g. smoothing, to improve the end image quality of the reconstruction for a selected set of conditions. In another embodiment, after a first preview image is selected, further preview images are generated and presented to the technician showing different outcomes for different sub-steps 218 or combination of sub-steps.

The AE 12 has at least two modes. In one mode, the AE 12 uses a lazy execution algorithm to generate preview images. The lazy execution algorithm generates preview images of slices in real time as the technician scrolls to look at more slices. A backend system 14 controls the acquisition and reconstruction of imaging data retrieved from a scan of the patient. The backend system 14 includes a resource scheduler 16 that manages anticipatory executions of reconstructions with a list of recommended sets of reconstruction parameters and the lifecycle or time to generate various additional images. Anticipatory executions are reconstruction parameters generated according to expected changes by the technician.

The backend system 14 also includes an execution engine 18 that executes a final reconstruction of scanned patient image data with the selected reconstruction parameters and sub-steps. The AE 12 during lazy execution responds to technician input, i.e. scrolling, and generates individual panel images of a single slice for each panel image. When the technician scrolls through a volume of the single slice images, other slices are generated immediately using the resource scheduler 16 to provide the technician with quick visual feedback and reduced computing effort. The AE 12 presents a technician with preview images representing recommended reconstruction parameters using a visual display 10. The visual display 10 includes the graphical interface 216 to receive a technician input, i.e. a user selection. The visual display 10 can be an LCD, TFT, LED, CRT or other screen implementations.

In another mode, the AE 12 uses an eager execution algorithm to generate the preview images. The technician selects a default set of reconstruction parameters and/or sub-steps of the patient data. Alternatively, the technician can select one of the recommended reconstruction parameters and/or sub-steps displayed to the technician as a preview image via the visual display 10. If technician selects the default set of reconstruction parameters, the preview images are generated in the background using the resource scheduler 16 to determine when computing resources are available. If the technician selects one of the recommended preview images, other preview images are also executed in the background using the resource scheduler 16 to determine when computing resources are available. The preview images are executed with the anticipation that the technician might change his mind and consider the recommended settings. If technician chooses one of the preview images reconstructed in the background, the results are already available. If the associated reconstruction of the patient data is not complete yet, the technician is notified via the visual display 10 and the resource scheduler 16 schedules the reconstruction to operate on the patient data and use the backend system 14 computing resources. In another embodiment, the preview images that are not viewed by the technician are stored in the database system 4 for a predefined or configured number of days after which they are deleted. When a final reconstruction is selected, an execution engine 18 of the backend system 14 controls scanning the patient 202 and the final reconstruction 220 of the scan image data according to the technician selected reconstruction settings, parameters, and/or sub-steps.

Figure 4:
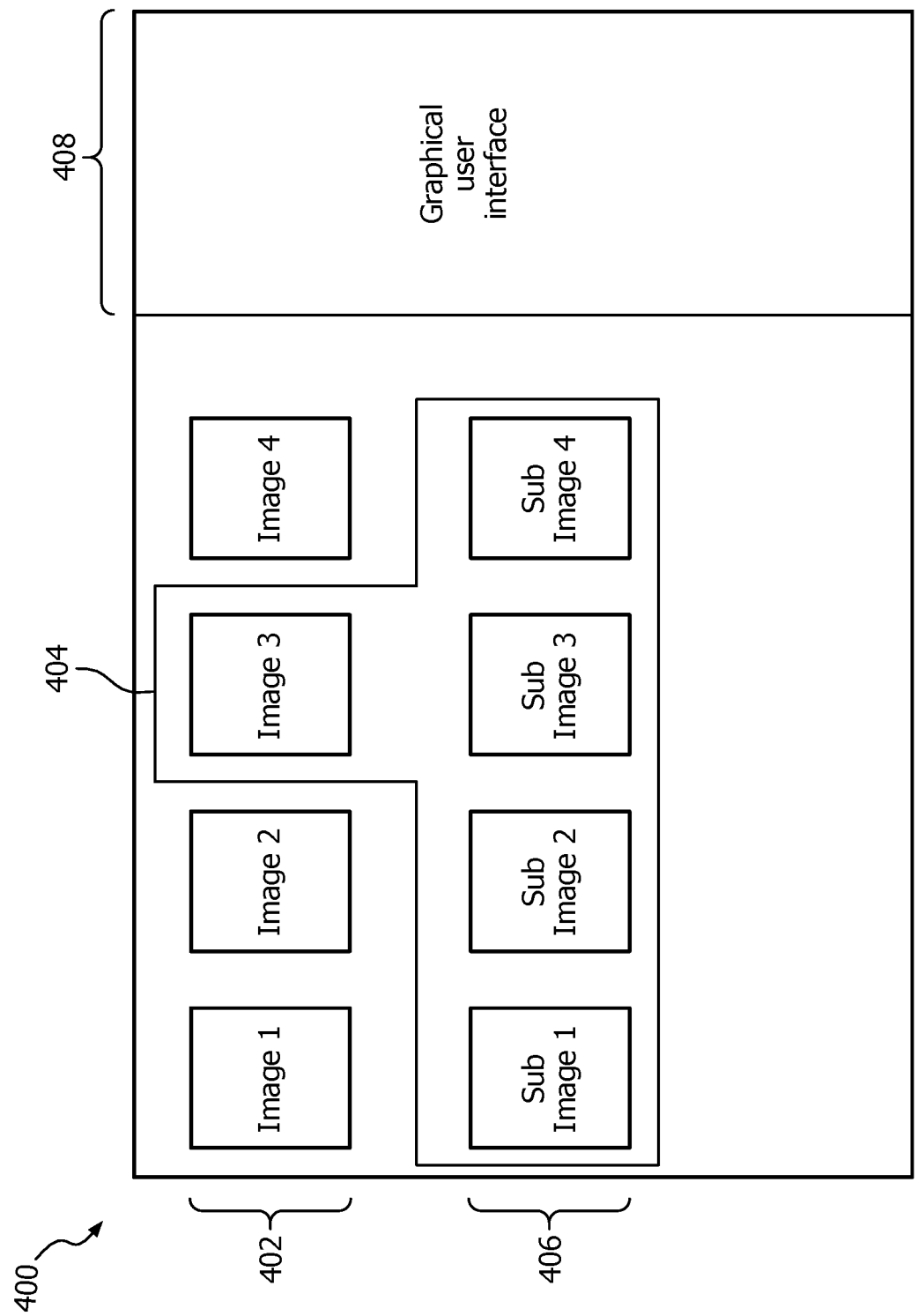
FIG. 4 depicts sample display of preview images and sub-step preview images displayed to a technician.

With reference to FIG. 4, an example display 400 of the graphical interface 216 displayed to the technician on a visual display 10 is shown. A top row 402 depicts preview images for recommended reconstruction parameters, sub-steps, and the like, where selection 404 of one of the preview images is displayed. From the selected preview image 404, sub-images 406 representing a variety of sub-step recommendations are displayed to the technician. The technician can make selections to change the proposed parameters, and sub-steps using a graphical user interface 408 displayed to the technician. In one embodiment, a new preview image is generated with the reconstruction parameters and sub-steps corresponding to the selected sub-image. Additional sub-images reconstructed with parameters and sub-steps similar to or at least partially different from the parameters and/or sub-steps corresponding to the new preview image. This preview can be iteratively repeated to refine and optimize the parameters and sub-steps. It is appreciated that the number of images display can be adapted depending on the size of the display and other factors. The top row 402 can display the best first images and the technician can optionally use a scroll function to view more images. The technician can also scroll to view more sub-images in row 406.

With reference to FIG. 5, an alternate modular view of an intelligent image reconstruction system contains a data collector 702 that compiles different types of data from a variety of sources and stores the collected data on a computer readable storage medium 704 or a database system 4. The data collector 702 compiles scan specific parameters 706 from a technician regarding the type of scan, the scan modality required and the like. The data collector 702 collects functional and anatomical limitations 707 for the desired scan of the patient from the technician. The data collector 702 stores patient histories 708 from all patients in an institution. The patient histories 708 include former scans and reconstructions that are used as preview images representing specific reconstruction parameters 709 and settings to achieve a reconstruction goal. The data collector 702 collects the patient's diagnosis 710 and/or prescription from the technician or the patient's medical file. The data collector 702 collects acquisition parameters 712 for the desired reconstruction of the patient image. The data collector 702 stores technician's preferences 714 that are received from an interactive GUI 716 or graphical interface 216 discussed in greater detail below. The technician preferences 714 includes a recordation of every selection and change to a reconstruction that a technician inputs. The technician preferences 714 are used to influence automated recommended reconstructions to be presented to the technician when planning subsequent reconstructions.

A data processor 718 processes the data from the data collector 702 to be used by the intelligent reconstruction system. The data processor 704 uses training elements 720 to adapt the intelligent reconstruction system according to the technician preferences 714. The training elements are driven by artificial intelligence that weights the technician preferences 714 and the other collected data to train the intelligent reconstruction system for use by a recommender module 722 or an AI engine 6 and AE 12.

The recommender module 722 uses the trained data from the data processor 718 to create and recommend reconstruction routes to the technician. The anticipation module accesses data from the data collector 702 via a neural network 724 and predicts future changes 726 to an initial reconstruction route that a technician might pursue. In one embodiment, the reconstruction routes are based on the technician's preferences history 714 stored with the data collector 702. In another embodiment, the recommended reconstruction route is based on an optimization, scan goals, patient demographics, and/or specific reconstruction parameters to be used. The recommender module 722 forecasts the resulting image quality 728 of a plurality of reconstruction routes and correlates the reconstruction routes to an exemplary preview image having the same reconstruction parameters.

The recommender module 722 processes the preview images to be displayed using the interactive GUI 716. The interactive GUI 716 displays the preview images on a display 10. As part of displaying of preview images, the interactive GUI 716 gives the technician various reconstruction editing tools to further change the reconstruction parameters. The tools are manipulated using the interactive GUI 716 that is configured to receive user input from the technician. The tools can be an options selector 730, feature controls 732, or normal/advanced user controls 734, 736. The interactive GUI 716 displays on a display 10 the different reconstruction routes that are forecasted by the recommender module 722. The interactive GUI 716 receives a final user selection of a reconstruction route. The recommender module 722 then processes scanned imaging data 740 of the patient into a final reconstructed image according to the selected reconstruction route. The recommender module 722 checks the reconstructed image for accuracy 742.

With reference to FIG. 6, different routes are displayed to the technician and detail tradeoffs associated with the routes going from a patient A 802 to the final reconstructed image 804. In one embodiment, the tradeoffs include image quality versus reconstruction time in relation to a default route. The routes detail specific tracers, reconstruction algorithms, and specific patient factors used for creating the route. For example, Route 1 806 is based on the specific tracer used, i.e. Tracer concentration X, that leads to a specific recommended reconstruction algorithm, i.e. reconstruction algorithm Y. The route 806 also details the tradeoff with a 20% improvement in image quality but the reconstruction time will take 3 extra minutes. Route 2 808 is based on patient demographics, i.e. the patient's weight, and a preliminary CT map to recommend number of iterations of a reconstruction algorithm and a specific frame overlap, i.e. 30%. The route 808 details a tradeoff of 35% reduction in reconstruction time with a 6% loss in image quality. Route 3 810 is based on a specific reconstruction goal, i.e. optimize for fastest reconstruction time, which the route suggests a reconstruction algorithm A and a single scatter simulation (SSS) algorithm H. The route 810 details a tradeoff of 30% loss in image quality but a 50% reduction in time with 35% resources used. It is appreciated that many different combinations of tradeoffs and route variations can be generated.

With reference to FIG. 7, a method 500 for intelligent reconstruction of patient imaging data is depicted. At a step 502, a patient is registered for an imaging scan. At a step 504, the database system 4 collects patient and scan data from various sources. At a step 506, the AI engine 6 recommends a default set of reconstruction parameters to the technician. At a step 508, the AE 12 generates alternate sets of reconstruction parameters. The alternate steps are anticipated changes a technician can make based on previous changes the technician has made to other reconstruction plans. At a step 510, preview images reconstructed with the alternate sets of reconstruction parameters are generated and displayed to the technician. The preview images can be images that are generated from other patients of similar physiological characteristics using various reconstruction parameters. At a step 512, a technician selection of a preview image is received via the visual display 10. At a step 513, the technician selection of the preview image is recorded and the collected data is updated with the selection for subsequent reconstructions. At a step 514, preview image and sub-images, i.e. images from the same scan data reconstructed with differing parameters and/or sub-steps, are generated and displayed to the technician. At a step 516, a technician selection of a sub-step preview image is received. The technician selection of the sub-step preview image is also recorded at a step 513 to update the collected data. At a step 518, an execution engine 18 scans the patient to get imaging data according to the set of reconstruction parameters represented by the preview image selection. At a step 520, the execution engine 18 reconstructs the imaging data according to the selected set of reconstruction parameters and/or sub-steps.

As used herein, a memory includes any device or system storing data, such as a random access memory (RAM) or a read-only memory (ROM). Further, as used herein, a processor includes any device or system processing input device to produce output data, such as a microprocessor, a microcontroller, a graphic processing unit (GPU), an application-specific integrated circuit (ASIC), a FPGA, and the like; a controller includes any device or system controlling another device or system, and typically includes at least one processor; a user input device includes any device, such as a mouse or keyboard, allowing a technician of the user input device to provide input to another device or system; and a display device includes any device for displaying data, such as a liquid crystal display (LCD) or a light emitting diode (LED) display.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A reconstruction system, having one or more processors configured to:
   select goals for a final image to be generated by reconstruction of image data of a patient, the goals including selecting one of: reconstruction algorithms, repetitions of iterative reconstruction algorithms, single scatter correction algorithms, single correction algorithms, and/or kernel size for post processing filter;
   generate initial reconstruction algorithms, reconstruction parameters, and/or sub-steps of the reconstruction for reaching the goals for the final image;
   access a database having data of at least one of: an electronic medical record of the patient, a patient diagnosis for the patient, and/or similar patient records for other patients similar to the patient; and
   refine the initial reconstruction algorithms, reconstruction parameters, and/or sub-steps of the reconstruction to generate alternative reconstruction algorithms, reconstruction parameters, and/or sub-steps of the reconstruction according to the accessed data of the database, where each meets the goals for the final image.

2. The reconstruction system according to claim 1, wherein the one or more processors are further configured to:
   match the alternative reconstruction algorithms, reconstruction parameters, and/or sub-steps of the reconstruction to similar patient records using a calculated similarity metric, wherein the similar patient records include reconstructed images for the other patients similar to the patient which are representative of the alternative reconstruction algorithms, reconstruction parameters, and/or sub-steps of the reconstruction; and
   display preview images for the alternative reconstruction algorithms, reconstruction parameters, and/or sub-steps of the reconstruction on a display where each reconstructed image is representative of the final image, wherein the preview images are the reconstructed images for the other patients similar to the patient.

3. The reconstruction system according to claim 1, wherein the one or more processors are further configured to:
   receive a selection of at least one different reconstruction algorithm, reconstruction parameter, and/or sub-step of the reconstruction from a technician; and
   record the change as a technician preference for the different reconstruction algorithm, reconstruction parameter, and/or sub-step of the reconstruction; and
   use a weighting toward the technician preference to anticipate future reconstruction algorithms, reconstruction parameters, and/or sub-steps of the reconstruction.

4. The reconstruction system according to claim 1, wherein the one or more processors are further configured to:
   receive a selection of a reconstructed image;
   generate and display further alternative reconstruction algorithms, reconstruction parameters, and/or sub-steps of the reconstruction according to the technician preferences;
   receive a subsequent selection of an alternative reconstructed image;
   reconstruct scanned imaging data of the patient into the final image according to the reconstruction algorithm, reconstruction parameter, and/or sub-steps specific to the selected reconstructed image to meet the selected goals.

5. A method for recommending reconstruction parameters, the method including:
   collecting data from a plurality of data sources;
   designing a patient specific reconstruction system to recommend a set of reconstruction parameters to a technician for reconstructing an image from the imaging scan of a patient based on the collected data;
   using the designed reconstruction system, generating a plurality of alternate sets of reconstruction parameters according to different reconstruction objectives, the reconstruction objectives including at least one of algorithmic additives, dynamic acquisition controls, technician preferences, and/or scan specific parameters;
   for each set of reconstruction parameters, generating a preview image for the set of reconstruction parameters, wherein the preview image depicts the expected image quality using sample images from a database that are associated with the set of reconstruction parameters;
   displaying the preview images on a display;
   receiving a selection of a preview image from a technician using the display whereby the corresponding set of reconstruction parameters is selected;
   and
   iteratively reconstructing imaging data according to the selected set of reconstruction parameters.

6. The method according to claim 5, including:
   updating a technician profile with the selection as a technician preferred selection on the database system, the technician profile including every selection made over time.

7. The method according to claim 5, including:
   after receiving a selection, generating and displaying sub-images on the display, the sub-images include alternative reconstruction algorithms, and sub-steps that show different tradeoffs between acquisition time and end image quality, and wherein the sub-images are based on the technician profile.

8. A reconstruction route generator for generating a route for reconstructing image data of a patient, including:
   a data collector configured to compile at least one of: scan specific data, physical attributes, acquisition parameters, technician preferences, diagnostic data, previous reconstruction data and/or previous reconstructed images representing reconstruction routes;
   a data processor configured to adapt the system according to the compiled data for a specific patient;
   a recommender module configured to use the trained data to create and predict a plurality of reconstruction routes, each reconstruction route anticipating a change to at least one reconstruction parameter affecting the final reconstruction of scanned patient imaging data, wherein the anticipation is based on optimization, a weighted technician preference, alternate algorithm, and/or alternate filter, and to access the data collector and correlate each generated reconstruction route with a previous reconstructed image of another patient other than the patient for which the route is being generated to use as a preview image of final reconstructed image quality; and an interactive GUI configured to display the plurality of reconstruction routes represented by the preview images to a user and further configured to accept a user input and to receive a preview image selection from a user.

9. The reconstruction route generator according to claim 8, wherein the interactive GUI is further configured to:
receive route alterations from a user including altered sub-steps of a recommended route; and displaying further preview images based on the received route alterations for the user to consider.

10. The reconstruction route generator according to claim 8, wherein the interactive GUI is configured to display each correlated preview image to the user with detailed description of reconstruction route parameters and tradeoffs in relation to a default reconstruction route.

11. The reconstruction route generator according to claim 8, wherein the recommender module is further configured to:
process scanned imaging data according to the reconstruction route correlated with the preview image selection;
process scanned imaging data according to each generated reconstruction route not selected when computing resources are available; and
store each processed reconstruction route with the data collector to be used for subsequent reconstructions.

12. The method according to claim 5, wherein the preview image is a reconstructed image for another patient different from but similar to the patient.

* * * * *